United States Patent [19]

Nakamura et al.

[11] Patent Number: 5,166,061
[45] Date of Patent: Nov. 24, 1992

[54] PROCESS FOR THE PRODUCTION OF 4-HALO-3-HYDROXYBUTYRONITRILE WITH CORYNEBACTERIUM OR MICROBACTERIUM

[75] Inventors: Tetsuji Nakamura; Fujio Yu; Ichiro Watanabe, all of Kanagawa, Japan

[73] Assignee: Nitto Chemical Industry Co. Ltd., Tokyo, Japan

[21] Appl. No.: 555,001

[22] Filed: Jul. 20, 1990

[30] Foreign Application Priority Data

Jul. 20, 1989 [JP] Japan .................... 1-185991

[51] Int. Cl.$^5$ .................... C12P 1/00; C12P 13/00; C12P 7/02; C12P 7/04; C12N 9/14
[52] U.S. Cl. .................... 435/128; 435/41; 435/155; 435/157; 435/195; 435/822; 435/843
[58] Field of Search ............ 435/41, 195, 128, 155, 435/157, 822, 843

[56] References Cited

U.S. PATENT DOCUMENTS 4,943,528  7/1990  Nakamura et al. ............ 435/158

OTHER PUBLICATIONS

Janssen et al. (1987) *Appl. Environ. Microbiol.* 53(3), 561–566 in *Chem. Abstr.*, 106(18), p. 328, Abst # 143413e.
Janssen et al. (1988) *Eur. J. Biochem.*, 171, 67–72.
Hardman et al. (1981) *J. Gen. Microbiol.*, 123, 117–128.
Bernhard (1968) "The Structure and Function of Enzymes", pp. 177–184, Benjamin, Menlo Park.

*Primary Examiner*—David M. Naff
*Assistant Examiner*—Jon P. Weber

[57] ABSTRACT

A process for the production of a 4-halo-3-hydroxybutyronitrile which comprises reacting a 1,3-dihalo-2-propanol with a dehalogenating enzyme originating from a Corynebacterium or a Microbacterium in the presence of an alkali cyanide to thereby convert the 1,3-dihalo-2-propanol into the 4-halo-3-hydroyxbutyronitrile and collecting the product thus formed is disclosed. According to this process, a 4-halo-3-hydroxybutyronitrile which is highly useful in the syntheses of various medicines and physiologically active substances can be easily and efficiently produced from an inexpensive starting material.

3 Claims, No Drawings

PROCESS FOR THE PRODUCTION OF 4-HALO-3-HYDROXYBUTYRONITRILE WITH CORYNEBACTERIUM OR MICROBACTERIUM

FIELD OF THE INVENTION

This invention relates to a process for the production of a 4-halo-3-hydroxybutyronitrile. More particularly, it relates to a process which comprises reacting 1,3-dihalo-2-propanol with a dehalogenating enzyme originating from a microorganism in the presence of an alkali cyanide to thereby biochemically produce a 4-halo-3-hydroxybutyronitrile.

A 4-halo-3-hydroxybutyronitrile, which has two functional groups different from each other, is useful as a starting material for the syntheses of various medicines and physiologically active substances. It is well known that this compound is useful, in particular, as a starting material for synthesizing L-carnitine (refer to JP-A-57-165352; the term "JP-A" as used herein means an "unexamined published Japanese patent application").

BACKGROUND OF THE INVENTION

Known processes for producing a 4-halo-3-hydroxybutyronitrile include the following:

(1) 1,3-Dichloro-2-propanol is reacted with an alkali cyanide in an aqueous solution under heating (refer to JP-B-36-21718; the term "JP-B" as used herein means an "examined Japanese patent publication").

(2) 3-Chloro-1,2-propanediol is treated with tosyl chloride so as to tosylate the alcohol at the 1-position. Next, the tosylated product is reacted with an alkali cyanide (refer to JP-A-57-165352).

(3) Epichlorohydrin is reacted with hydrocyanic acid in the presence of a catalytic amount of potassium cyanide [refer to F. Binon et al., Bull. Soc. Chim. Belges, 72, 166–177 (1963)].

However, the process (1) can give only a limited yield (i.e., approximately 40%). The process (2) requires a complicated reaction procedure involving two stages and gives a low total yield (i.e., approximately 45%). On the other hand, it is difficult to control the reaction conditions for the process (3), wherein a dangerous chemical (i.e., hydrocyanic acid) is employed, so as to prevent the formation of side products. Thus, none of these known processes is advantageous from an industrial viewpoint. Furthermore, each of the processes (1) to (3) is a chemical one whereby no optically active product can be obtained from a prochiral or racemic starting material.

SUMMARY OF THE INVENTION

Under these circumstances, the present inventors have paid their attention to the usefulness of a 4-halo-3-hydroxybutyronitrile, in particular, an optically active one as an intermediate in the syntheses of various medicines. As a result of extensive investigation on a process for the production of a 4-halo-3-hydroxybutyronitrile, the present inventors have established a novel process by utilizing the enzymatic effect of a microorganism. Accordingly, the present invention provides a process for the production of a 4-halo-3-hydroxybutyronitrile which comprises reacting a 1,3-dihalo-2-propanol with a dehalogenating enzyme originating from a microorganism in the presence of an alkali cyanide to thereby convert said 1,3-dihalo-2-propanol into the target 4-halo-3-hydroxybutyronitrile and then collecting the product thus formed.

An enzyme capable of converting a halogen group into a hydroxyl group is generally known as a dehalogenating enzyme [refer to *Koso Handbook* (Enzyme Handbook), 627 (Asakura Shoten); and T. Yokota et al., *Agric. Biol. Chem.*, Vol 50, 453–460 (1986)]. However, no reaction for the conversion of a 1,3-dihalo-2-propanol, used as a substrate, into a 3-halo-1,2-propanediol had been known until discovered by the present inventors. Thus, the present inventors have previously applied for a patent (refer to Japanese Patent Application No. 1-100173). Subsequently, the present inventors have further discovered that the above-mentioned enzyme can surprisingly convert a halogen group of a 1,3-dihalo- 2-propanol not into a hydroxyl group, but into a nitrile group when used in the presence of an alkali cyanide, thus completing the present invention. According to the process of the present invention, the reaction can be highly efficiently carried out at ordinary temperature and at a mild pH value (almost neutral). Therefore, the process of the present invention is advantageous, compared with the conventional chemical processes. Furthermore, the process of the present invention makes it possible for the first time to produce an optically active R(−)-4-halo-3-hydroxybutyronitrile from a 1,3-dihalo-2-propanol, which is an inexpensive prochiral compound.

DETAILED DESCRIPTION OF THE INVENTION

The term "dehalogenating enzyme" as used herein means an enzyme which can finally convert a halogen atom in a 1,3-dihalo-2-propanol into a nitrile group. Particular examples thereof include those produced by microorganisms which were isolated and identified by the present inventors for the first time (for example, Strains N-653 and N-1074 belonging to the genus Corynebacterium, Strain N-4701 belonging to the genus Microbacterium). These microorganisms have been deposited with the Fermentation Research Institute, Agency of Industrial Science and Technology, Ministry of International Trade and Industry, Japan under the accession number FERM P-10390, after conversion to deposition under Budapest Treaty, FERM BP-2642 (Corynebacterium sp. N-653), the accession number FERM P-10391, after conversion to deposition under Budapest Treaty, FERM BP-2643 (Corynebacterium sp. N-1074) and the accession number FERM P-10674, after conversion to deposition under Budapest Treaty, FERM BP-2644 (Microbacterium sp. N-4701). The microorganisms have been accepted by the following international depository authority: Fermentation Research Institute, Agency of Industrial Science and Technology, Ministry of International Trade and Industry, Japan at 1-3, Higashi 1-chome, Tsukuba-shi, Ibaraki, Japan.

The dates of deposit are as follows:

|  | N-653 | N-1074 | N-4701 |
| --- | --- | --- | --- |
| Date of an original deposit | Number 10, '88 (FERM P-10390) | November 10, '88 (FERM p-10391) | April 19, '89 (FERM P-10674) |

-continued

|  | N-653 | N-1074 | N-4701 |
|---|---|---|---|
| Date on which the deposit was transferred to deposition under Budapest Treaty | Novemer 8, '89 (FERM BP-2642) | November 8, '89 (FERM BP-2643) | November 8, '89 (FERM BP-2644) |

The mycological properties of these strains are as follows. Strain N-653
Morphology: polymorphic bacillus.
Peripheral cell of colony: not extended.
Gram-stain: +.
Acid-fastness: —.
Spore: not observed.
Motility: +.
Oxidase: —.
Catalase: +.
OF: Oxydative.
Growth under anaerobic condition: —.
meso-Diaminopimellic acid in hydrolysate of whole cell: —.
Diamino acid in cell wall: diaminobutyric acid.
Glycolyl test: — (acetyl type).
Decomposition of starch: —.
Liquefaction of gelatin: +.
Decomposition of cellulose: —.
Decomposition of urea: —.
Thermal resistance in skim milk medium 30 min. at 63° C.: —.
Thermal resistance in skim milk medium 15 min. at 72° C.: —.
 Strain N-1074
Morphology: polymorphic bacillus.
Peripheral cell of colony: not extended.
Gram-stain: +.
Acid-fastness: —.
Spore: not observed.
Motility: +.
Oxidase: —.
Catalase: +.
OF: Oxydative.
Growth under anaerobic condition: —.
meso-Diaminopimellic acid in hydrolysate of whole cell: —.
Diamino acid in cell wall: diaminobutyric acid.
Glycolyl test: — (acetyl type).
Decomposition of starch: +.
Liquefaction of gelatin: —.
Decomposition of cellulose: —.
Decomposition of urea: —.
Thermal resistance in skim milk medium 30 min. at 63° C.: —.
Thermal resistance in skim milk medium 15 min. at 72° C.: —.
 Strain N-4701
Morphology: polymorphic bacillus.
Peripheral cell of colony: not extended.
Gram-stain: +.
Spore: not observed.
Motility: +.
Flagellum: polar to side.
Colony color: yellowish orange.
Oxidase: +.
Catalase: +.
OF: Oxydative.
Growth under anaerobic condition: —.
meso-Diaminopimellic acid in hydrolysate of whole cell: —.
Diamino acid in cell wall: lysine.
Glycolyl test: + (glycolyl type).
Decomposition of starch: +.
Liquefaction of gelatin: —.
Reduction of nitrate: —.
Utilization of arginine: +.
Production of hydrogen sulfide: —.
Decomposition of urea: —.
Thermal resistance in skim milk medium 30 min. at 60° C.: —.
Production of acid:
 Inulin: +.
 Glycerol: —.
 Glucose: +.
 Sucrose: +.
 Trehalose: +.
 Raffinose: +.

Based on these mycological properties, Strain N-653 and Strain N-1074 were regarded to belong to the genus Corynebacterium while Strain N-4701 was regarded to belong to the genus Microbacterium, in accordance with *Bergy's Manual of Systematic Bacteriology*, Vol. 2 (1986).

In order to culture these strains, any media may be employed so long as they can grow therein. For example, a carbon source may be selected from among saccharides such as glucose, fructose, sucrose and maltose, organic acids such as acetic acid and citric acid and alcohols such as ethanol and glycerol. A nitrogen source may be selected from among natural materials such as peptone, meat extract, yeast extract, protein hydrolysates and amino acids and various inorganic and organic ammonium salts. Furthermore, the medium may contain inorganic salts, trace metals and vitamins, if required. In order to elevate the activity of the enzyme, it is effective to add, for example, 1,3-dichloro-2-propanol or 3-chloro-1,2-propanediol to the medium.

The above-mentioned microorganisms may be cultured in a conventional manner, for example, at a pH of from 4 to 10 and at 20° to 40 C. under aerobic conditions for 10 to 96 hours.

The 1,3-dihalo-2-propanol to be used in the present invention may be selected from among, for example, 1,3-dichloro-2-propanol and 1,3-dibromo-2-propanol. The alkali cyanide may be selected from among, for example, potassium cyanide and sodium cyanide.

A 4-halo-3-hydroxybutyronitrile may be obtained by reacting a 1,3-dihalo-2-propanol with the dehalogenating enzyme as follows.

The substrate and the alkali cyanide, which will be called "the substrate, etc." hereinafter, may be added to the microbial culture broth obtained by the above-mentioned method or a cell suspension obtained by centrifuging the culture broth. Alternately, the substrate etc. may be added to a suspension or solution of treated cells (for example, disrupted cells, cell extract or crude or purified enzyme), or a suspension of the cells or treated cells immobilized in a conventional manner. Alternately, the substrate etc. may be added to the culture broth during the culture period so as to simultaneously sustain the culture and the enzymatic reaction.

The concentration of the substrate in the reaction mixture is not particularly limited. The concentration may preferably range from 0.1 to 10% (w/v). The alkali cyanide may be usually added in an amount one to three times (by mol) as much as the substrate. The substrate etc. may be added either at once or by portions.

In case of using the cell per se, the cell concentration in the reaction mixture is usually from 0.01 to 10% (w/v).

It is preferable to effect the reaction at a temperature of from 5° to 50 C. and at a pH value of from 4 to 10.

The reaction time may vary depending on the concentrations of the substrate etc. and cells and other reaction conditions. It is generally preferable to select the reaction conditions in such a manner as to complete the reaction within 1 to 120 hours.

The 4-halo-3-hydroxybutyronitrile thus formed and accumulated in the reaction mixture may be then collected and purified in a conventional manner. For example, the cells are separated from the reaction mixture by, for example, centrifugation and then extracted with a solvent such as ethyl acetate. Next, the solvent is distilled off under reduced pressure to thereby give the 4-halo-3-hydroxybutyronitrile in the form of a syrup. This syrup may be further purified by distilling under reduced pressure.

The present invention will now be illustrated in greater detail by way of the following Examples, but it should be understood that the present invention is not construed as being limited thereto.

EXAMPLE 1

The pH value of an aqueous medium comprising 1% of glucose, 0.5% of peptone, 0.3% of meat extract and 0.3% of yeast extract was adjusted to 7.0. 100 ml portions of this medium were pipetted into 500 ml Erlenmeyer flasks (#) and pasteurized at 120 C. for 15 minutes. Then, 0.8 ml of a 25% (w/v) aqueous solution of 3-chloro-1,2-propanediol, which had been sterilized with a membrane filter, was added.

These media were inoculated with the strains N-653 and N-1074 respectively. These strains were cultured therein at 30 C. under shaking for 48 hours. Each culture broth was centrifuged and the cells thus collected were washed with 100 ml of a 100 mM phosphate buffer solution once. The cells were suspended in 100 ml of a solution containing 0.5% (w/v) of 1,3-dichloro-2-propanol and 0.5% (w/v) of potassium cyanide (in 1M phosphate buffer solution, pH 7.8) and allowed to react at 20 C. for 22 to 23 hours under stirring.

After the completion of the reaction, the cells were removed from the reaction mixture and the 4-chloro-3-hydroxybutyronitrile thus formed in the supernatant was determined with gas chromatography. Consequently, the yields of this product based on the substrate were 25.8% and 78.5%, respectively.

EXAMPLE 2

A medium obtained in the same manner as the one described in Example 1 was inoculated with the strain N-4701 which was then cultured therein at 30 C. for 48 hours under shaking. 80 ml of this culture broth was centrifuged. The cells thus collected were washed with 80 ml of a 100 mM tris HCl buffer solution (pH 8.0) once and suspended in 40 ml of a solution containing 1.0% (w/v) of 1,3-dichloro-2-propanol and 0.5% (w/v) of sodium cyanide (1M tris HCl buffer solution, pH 8.0). Then, the reaction was conducted at 20 C. for 20 hours under stirring.

After the completion of the reaction, the cells were removed from the reaction mixture and the 4-chloro-3-hydroxybutyronitrile thus formed in the supernatant was determined by gas chromatography. As a result, the yield of the product based on the substrate was 80%.

EXAMPLE 3

A medium obtained in the same manner as the one described in Example 1 was inoculated with the strain N-1074 which was then cultured therein at 30° C. for 48 hours under shaking. 500 ml of this culture broth was centrifuged and the cells thus collected were washed with a 20 mM phosphate buffer solution (pH 7.0) containing 5 mM mercaptoethanol. The washed cells were suspended in 50 ml of the same phosphate buffer solution as above and then disrupted with a French Press operating at 1,300 kg/cm$^2$. The debris was removed by centrifugation at 15,000×g for 30 min. Then, 10 ml of the resulting supernatant was reacted as crude enzyme solution with a solution containing 0.5 g of 1,3-dichloro-2-propanol and 0.35 g of potassium cyanide (KCN) (in 40 ml of 1M phosphate buffer solution, pH 8.0) at 20° C. for 10 hours.

After the completion of the reaction, the 4-chloro-3-hydroxybutyronitrile thus formed was determined by gas chromatography. As a result, the yield of the product based on the substrate was 82.5%.

While the invention has been described in detail and with reference to specific embodiments thereof, it will be apparent to one skilled in the art that various changes and modifications can be made therein without departing from the spirit and scope thereof.

What is claimed is:

1. A process for the production of 4-halo-3-hydroxybutyronitrile which comprises reacting 1,3-dihalo-2-propanol with a dehalogenating enzyme originating from a microorganism selected from the group consisting of Corynebacterium sp. N-653 (FERM BP-2642), Corynebacterium sp. N-1074 (FERM BP-2643); and Microbacterium sp. N-4701 (FERM BP-2644) in the presence of an alkali cyanide to thereby convert said 1,3-dihalo-2-propanol into 4-halo-3-hydroxybutyronitrile and collecting the product thus formed.

2. A process as in claim 1, wherein the 1,3-dihalo-2-propanol is initially present in the reaction mixture in an amount of 0.1 to 10 g/100 ml.

3. A process as in claim 1, wherein the amount of alkali cyanide is 1 to 3 molar times the amount of the 1,3-dihalo-2-propanol.

* * * * *